United States Patent
Shneider

(10) Patent No.: US 11,857,668 B1
(45) Date of Patent: Jan. 2, 2024

(54) UNDERARM TONER

(71) Applicant: Diana Shneider, Los Angeles, CA (US)

(72) Inventor: Diana Shneider, Los Angeles, CA (US)

(73) Assignee: BELLA ORGANIC SKIN, INC, Los Angeles, CA (US)

( * ) Notice: Subject to any disclaimer, the term of this patent is extended or adjusted under 35 U.S.C. 154(b) by 0 days.

(21) Appl. No.: 17/686,198

(22) Filed: Mar. 3, 2022

(51) Int. Cl.
| | |
|---|---|
| *A61K 8/9789* | (2017.01) |
| *A61K 8/9794* | (2017.01) |
| *A61K 8/34* | (2006.01) |
| *A61K 8/99* | (2017.01) |
| *A61K 8/365* | (2006.01) |
| *A61K 8/9783* | (2017.01) |
| *A61Q 15/00* | (2006.01) |

(52) U.S. Cl.
CPC ............ *A61K 8/9789* (2017.08); *A61K 8/345* (2013.01); *A61K 8/365* (2013.01); *A61K 8/9783* (2017.08); *A61K 8/9794* (2017.08); *A61K 8/99* (2013.01); *A61Q 15/00* (2013.01); *A61K 2800/30* (2013.01)

(58) Field of Classification Search
None
See application file for complete search history.

(56) References Cited

PUBLICATIONS

Foley "This Underarm Toner Will Get Rid of the Funk Your Natural Deodorant Can't", InStyle, an internet article published on Apr. 9, 2021 (and obtained from the website: https://www.instyle.com/beauty/skin/best-natural-deodorant-bella-skin-watermelon-probiotic-underarm-toner-review) (Year: 2021).*

"Bella Skin Beauty-Watermelon Probiotic Underarm Toner 55 ml" Alaina Natural Beauty, which is an internet article obtained from the website: https://www.alainanaturalbeauty.com/shop-1/bellaskinbeautywatermelonprobioticunderarmtoner. (at least before Apr. 9, 2021).*

Dr. Josh Axe ("14 Geranium Oil Uses & Benefits for Healthy Skin and Much More", an internet article published on Jun. 26, 2018 and obtained from the website: https://draxe.com/essential-oils/geranium-oils/) (2018).*

Dr. Josh Axe ("Cinnamon Oil: 10 Proven Benefits and Uses", an internet article published on Jul. 25, 2018 and obtained from the website: . https://draxe.com/essential-oils/cinnamon-oil/ ) (2018).*

Facebook website screen shots obtained from https://www.facebook.com/bellaskinbeauty1/ (dated Mar. 12, 2021).*

"Organic Skin Japan Intensive Whitening Underarm Toner (60ml) Armpit Whitener with Sunflower Oil" obtained from https:// organicskin.jp/products/organic-skin-japan-intensive-whitening-underarm-toner-60ml-armpit-whitener-with-sunflower-oil (date unknown).*

"Bliss What a Melon Replenishing Watermelon Toner - 7 Fl Oz" obtained from amazon.com webpage (date unknown).*

"Glycolic Acid 7% Toning Solution" obtained from https://theordinary.com/en-US/glycolic-acid-7-toning-solution-exfoliator-100418. html (date unknown).*

* cited by examiner

*Primary Examiner* — Sin J Lee
(74) *Attorney, Agent, or Firm* — Plager Schack LLP; Mark H. Plager; Kara Verryt

(57) ABSTRACT

An underarm toner for eliminating or reducing odor-causing bacteria may include rosa damascena; water; aloe leaf juice; calendula; lemon balm; glycerin; ylang-ylang; lactic acid; *lactobacillus* and coconut fruit extract; *lactobacillus* ferment; watermelon fruit extract; chamomile extract; a probiotic blend; grapefruit seed extract; sandalwood oil; lavender oil; rosemary oil; clary sage oil; eucalyptus oil; lemon peel oil; red radish root; geranium oil; and cinnamon leaf oil. A method for eliminating body odor may include applying the underarm toner to the underarm region, causing the pH level to be maintained at about 4 to about 5, thus eliminating odor-causing bacteria from the underarm region.

5 Claims, No Drawings

UNDERARM TONER

BACKGROUND

The embodiments described herein relate generally to toiletries and, more particularly, to an underarm toner that eliminates odor-causing bacteria.

Many individuals suffer from body odor, particularly body odor that emanates from the underarm. Body odor is caused by a bacteria overgrowth in the alkaline underarm environment.

Currently, body odor is typically dealt with by applying deodorant, which often has to be re-applied throughout the day to keep people fresh and smelling good. However, deodorants simply temporarily mask the odor; they do not eliminate odor-causing bacteria. As such, the bacteria continues to breed, creating more odor. Moreover, existing deodorants tend to include irritating, harmful, and/or hormone-altering ingredients, such as aluminum, alcohol, and coconut oil.

Therefore, what is needed is an underarm toner that can eliminate the odor-causing bacteria by establishing a proper pH level to provide for a fresh and odor-free day for a user, wherein the toner is free of harsh hormone-altering chemicals and commonly known skin irritants.

SUMMARY

Some embodiments of the present disclosure include an underarm toner for eliminating or reducing odor-causing bacteria may include rosa damascena; water; aloe leaf juice; calendula; lemon balm; glycerin; ylang-ylang; lactic acid; *lactobacillus* and coconut fruit extract; *lactobacillus* ferment; watermelon fruit extract; chamomile extract; a probiotic blend; grapefruit seed extract; sandalwood oil; lavender oil; rosemary oil; clary sage oil; eucalyptus oil; lemon peel oil; red radish root; neroli oil; sweet orange oil; geranium oil; and cinnamon leaf oil. A method for eliminating body odor may include applying the underarm toner to the underarm region, causing the pH level to be maintained at about 4 to about 5, thus eliminating odor-causing bacteria from the underarm region.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

The composition of the present disclosure may be used as an underarm toner for eliminating body odor and may comprise the following elements. This list of possible constituent elements is intended to be exemplary only, and it is not intended that this list be used to limit the composition of the present application to just these elements. Persons having ordinary skill in the art relevant to the present disclosure may understand there to be equivalent elements that may be substituted within the present disclosure without changing the essential function or operation of the composition.

The various elements of the present disclosure may be related in the following exemplary fashion. It is not intended to limit the scope or nature of the relationships between the various elements, and the following examples are presented as illustrative examples only.

By way of example, some embodiments of the present disclosure include an underarm toner for eliminating or reducing odor-causing bacteria, wherein the underarm toner comprises nature-derived ingredients. More specifically, the underarm toner may comprise rose water (i.e., rosa damascena), water, aloe leaf juice, calendula, lemon balm, glycerin, ylang-ylang, lactic acid, *lactobacillus* and coconut fruit extract, *lactobacillus* ferment, watermelon fruit extract, chamomile extract, a probiotic blend, grapefruit seed extract, sandalwood oil, lavender oil, rosemary oil, clary sage oil, eucalyptus oil, lemon peel oil, red radish root, geranium oil, and cinnamon leaf oil, wherein the underarm toner maintains the skin's pH level at, for example, about 4 to about 5 to prevent the odor-causing bacteria from growing and proliferating.

In a particular embodiment, the underarm toner of the present disclosure may comprise about 19 to about 23 volume % (vol. %) rosa damascena, about 15 to about 19 vol. % water, about 7 to about 9 vol. % aloe leaf juice, about 1 to about 3 vol. % calendula, about 1 to about 3 vol. % lemon balm, about 1 to about 3 vol. % glycerin, about 1 to about 2 vol. % ylang ylang, about 3 to about 5 vol. % lactic acid, about 2 to about 4 vol. % *lactobacillus* and coconut fruit extract, about 2 to about 4 vol. % *lactobacillus* ferment, about 0.3 to about 0.6 vol. % watermelon fruit extract, about 0.3 to about 0.6 vol. % chamomile extract, about 0.08 to about 0.09 vol. % probiotic blend, about 0.2 to about 0.4 vol. % grapefruit seed oil, about 0.01 to about 0.02 vol. % sandalwood oil, about 0.001 to about 0.01 vol. % lavender oil, about 0.001 o about 0.01 vol. % rosemary oil, about 0.001 to about 0.01 vol. % clary sage oil, about 0.01 to about 0.02 vol. % eucalyptus oil, about 0.001 to about 0.01 vol. % lemon peel oil, about 0.001 to about 0.01 vol. % geranium oil, about 0.01 to about 0.02 vol. % cinnamon leaf oil, and about 0.5 to about 0.75 vol. % red radish root.

In embodiments, the probiotic blend may comprise *Bacillus coagulans, Lactobacillus rhamnosus, Lactobacillus acidophilus, Bifidobacterium bifidum, Bifidobacterium longum, Lactobacillus casei*, and *Streptococcus thermophiles*. For example, in a particular embodiment, the probiotic blend may comprise each of the ingredients combined in equal volumes. Thus, the volume ratio of each ingredient to each other ingredient may be about 1:1. In embodiments, the probiotic blend may increase the activity and growth of beneficial skin microbiota.

To create the underarm toner of the present disclosure, the ingredients may simply be combined and blended to emulsify the toner.

To use the underarm toner of the present disclosure, a user may apply 2 to 3 sprays of the toner under each arm and gently wipe off the excess liquid with a cotton round or a tissue. The user may then follow with their favorite deodorant. Because the combination of the ingredients in the toner creates a pH level of about 4 to about 5, such as 4.5, the body odor-causing bacterial is eliminated, leaving the underarm skin at a slightly acidic pH. As such, bacteria is not able to grow for at least 24 hours. Because it is the bacteria that creates the body odor and because using the underarm toner of the present disclosure will free the underarm of the bacteria, when deodorant is applied on top of the skin treated with the toner, the user will stay fresh all day or longer.

As evidenced by the above description of the toner, the underarm toner of the present disclosure is free of aluminum, alcohol, and coconut oil, each of which can have negative health effects when applied to the underarm.

The above-described embodiments of the invention are presented for purposes of illustration and not of limitation.

While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. An underarm toner for eliminating or reducing odor-causing bacteria, the underarm toner comprising:
    rosa damascena;
    water;
    aloe leaf juice;
    calendula;
    lemon balm;
    glycerin;
    ylang-ylang;
    lactic acid;
    *lactobacillus* and coconut fruit extract;
    *lactobacillus* ferment;
    watermelon fruit extract;
    chamomile extract;
    a probiotic blend;
    grapefruit seed extract;
    sandalwood oil;
    lavender oil;
    rosemary oil;
    clary sage oil;
    eucalyptus oil;
    lemon peel oil;
    red radish root; geranium oil; and cinnamon leaf oil.

2. The underarm toner of claim 1, wherein the underarm toner is configured to maintain an underarm skin's pH level at about 4 to about 5.

3. The underarm toner of claim 1, wherein the probiotic blend comprises *Bacillus coagulans, Lactobacillus rhamnosus, Lactobacillus acidophilus, Bifidobacterium bifidum, Bifidobacterium longum, Lactobacillus casei*, and *Streptococcus thermophiles*.

4. The underarm toner of claim 1, wherein the under arm toner comprises:
    about 19 to about 23 volume % (vol. %) rosa damascena;
    about 15 to about 19 vol. % water;
    about 7 to about 9 vol. % aloe leaf juice;
    about 1 to about 3 vol. % calendula;
    about 1 to about 3 vol. % lemon balm;
    about 1 to about 3 vol. % glycerin;
    about 1 to about 2 vol. % ylang ylang;
    about 3 to about 5 vol. % lactic acid;
    about 2 to about 4 vol. % *lactobacillus* and coconut fruit extract;
    about 2 to about 4 vol. % *lactobacillus* ferment;
    about 0.3 to about 0.6 vol. % watermelon fruit extract;
    about 0.3 to about 0.6 vol. % chamomile extract;
    about 0.08 to about 0.09 vol. % probiotic blend;
    about 0.2 to about 0.4 vol. % grapefruit seed oil;
    about 0.01 to about 0.02 vol. % sandalwood oil;
    about 0.001 to about 0.01 vol. % lavender oil;
    about 0.001 o about 0.01 vol. % rosemary oil;
    about 0.001 to about 0.01 vol. % clary sage oil;
    about 0.01 to about 0.02 vol. % eucalyptus oil;
    about 0.001 to about 0.01 vol. % lemon peel oil;
    about 0.001 to about 0.01 vol. % geranium oil;
    about 0.01 to about 0.02 vol. % cinnamon leaf oil; and
    about 0.5 to about 0.75 vol. % red radish root.

5. The underarm toner of claim 1, wherein the toner is free of aluminum, alcohol, and coconut oil.

* * * * *